United States Patent
Sengupta et al.

(10) Patent No.: US 7,060,820 B1
(45) Date of Patent: Jun. 13, 2006

(54) PROCESS FOR MAKING CAPROLACTAM

(75) Inventors: Sourav K. Sengupta, Wilmington, DE (US); John J. Ostermaier, Orange, TX (US); Gregory S. Kirby, Avondale, PA (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 11/083,728

(22) Filed: Mar. 18, 2005

(51) Int. Cl.
*C07D 201/02* (2006.01)

(52) U.S. Cl. .................................................. 540/539
(58) Field of Classification Search ................. 540/539
See application file for complete search history.

(56) References Cited

U.S. PATENT DOCUMENTS

| 2,301,964 A | 11/1942 | Martin |
| 2,357,484 A | 9/1944 | Martin |
| 6,069,246 A | 5/2000 | Chiarelli et al. |
| 6,353,101 B1 | 3/2002 | Eiermann et al. |
| 6,686,465 B1 * | 2/2004 | Ohlbach et al. ............ 540/539 |

* cited by examiner

*Primary Examiner*—Bruck Kifle

(57) ABSTRACT

Lactams, in particular ε-caprolactam, are produced by the hydrolytic cyclization of aminonitriles, in particular 6-aminocapronitrile, in the vapor phase in a plurality of adiabatic fixed bed reaction zones arranged in succession wherein at least a portion of the heat of the exothermic reaction is removed between each of the successive reaction zones. Conducting the reaction in such a manner requires less capital for the reactor itself. It has also been found that the product exiting such a reaction system can be directly fed to a distillation unit without the need of additional cooling or storing.

24 Claims, No Drawings

PROCESS FOR MAKING CAPROLACTAM

FIELD OF THE INVENTION

The present invention relates to the field of production of lactams from aminonitriles, and in particular to the production of ε-caprolactam by the vapor phase hydrolytic cyclization of 6-aminocapronitrile.

BACKGROUND OF THE INVENTION

ε-Caprolactam is a precursor for the preparation of Nylon-6. Nylon-6 was first made in 1899 by heating 6-aminohexanoic acid. Commercially feasible synthesis of Nylon-6 from ε-caprolactam was discovered by Paul Schlack at I. G. Farbenindustrie in 1938. Currently, approximately 95% of the world's ε-caprolactam is produced from cyclohexanone oxime via the Beckmann rearrangement. The starting material for cyclohexanone can be cyclohexane, phenol, or benzene. Through a series of reductions and/or oxidations, cyclohexanone is formed. The latter is then reacted with a hydroxylamine salt usually the sulfate, to form the oxime and ammonium sulfate. The oxime is rearranged in concentrated sulfuric acid, and the resulting lactam sulfate salt is neutralized with ammonia to form ε-caprolactam and additional ammonium sulfate. Subsequently, pure ε-caprolactam is obtained through numerous separation and purification steps. The current process is extremely capital intensive and generates large quantities of waste.

An economically attractive method of production of caprolactam uses 6-aminocapronitrile as a precursor. U.S. Pat. No. 2,301,964 (E. I. Du Pont de Nemours & Company) discloses a liquid-phase method of producing lactams from aminonitriles and water. Hydrolysis and concurrent lactam formation proceed rapidly when aminonitrile is reacted in a weak aqueous solution. Temperatures of from about 200° C. to about 375° C. are employed. The aminonitrile and water are maintained at this reaction temperature for not more than 1 hour. The reaction is preferably catalyzed with hydrogen sulfide.

U.S. Pat. No. 2,357,484 (E. I. Du Pont de Nemours & Company) discloses a vapor-phase catalytic process for preparing N-substituted amides comprising passing a vaporized mixture of water and an aliphatic aminonitrile, containing at least one aminonitrile moiety, over a dehydration-type catalyst at a temperature of typically from about 150° C. to about 500° C. for not more than 1 minute. When an open-chain aliphatic aminonitrile is used, in which the amino and nitrile groups are separated by at least two carbon atoms in contiguous relation, the product obtained is a lactam.

U.S. Pat. No. 6,353,101 (BASF) discloses the hydrolytic cyclization of aminonitriles, 6-aminocapronitrile in particular, to lactams, ε-caprolactam in particular, in the vapor phase using metal oxide catalysts. The use of a single bed or a single bed divided into several trays with addition of reactants or inert gases has been disclosed. Additionally, the use of one or more reaction chambers, such as a multitubular reactor, has been suggested.

U.S. Pat. No. 6,069,246 (Rhodia) discloses a method of production of caprolactam from 6-aminocapronitrile and water by vapor phase hydrolytic cyclization, followed by purification of the caprolactam by distillation. In order to prevent formation of oligomers during the distillation step in the method, the product of reaction of 6-aminocapronitrile and water is cooled down to a temperature below about 150° C. and, if necessary, kept in storage before it is distilled. Both cooling and storage increases capital and operating cost of the process.

It would, therefore, be desirable to have a process of producing caprolactam from 6-aminocapronitrile in which no cooling or storage is required before distillation. The present invention provides such a process.

SUMMARY OF THE INVENTION

Lactams, in particular ε-caprolactam, are produced according to the invention by the hydrolytic cyclization of aminonitriles, in particular 6-aminocapronitrile, in the vapor phase in a plurality of successive adiabatic fixed bed reaction zones wherein at least a portion of the heat of the exothermic reaction is removed between each of the successive reaction zones. Conducting the reaction in such a manner requires less capital for the reactors. It has also been found that the product exiting such a reaction system can be directly fed to a distillation unit without the need of additional cooling or storing. The invention is, therefore, a process for preparing ε-caprolactam by the hydrolytic cyclization of 6-aminocapronitrile in the vapor phase, said process comprising contacting a superheated mixture of 6-aminocapronitrile vapor and steam with a catalyst in a plurality of successive adiabatic reaction zones, wherein the superheated vapor mixture is fed into a first reaction zone and a final reaction product comprising caprolactam is removed from a final reaction zone, wherein further an intermediate reaction product is removed from each reaction zone prior to the final reaction zone, cooled and then fed into the next reaction zone; and separating the caprolactam from the final reaction product by distillation.

DETAILED DESCRIPTION OF THE INVENTION

The present invention involves the preparation and separation of a lactam by the reaction of an aliphatic aminonitrile with water in the presence of a solid acid catalyst, the aliphatic aminonitrile having the general formula (1):

$$N{\equiv}C{-}R{-}NH_2 \qquad (I)$$

is in which R is an alkylene group having 3 to 12 carbon atoms. The preferred compound of formula (I) is 6-aminocapronitrile (ACN), which produces ε-caprolactam (CPL), the polymerization of which leads to the synthesis of Nylon-6.

In a system that is one embodiment of the present invention a stream of 6-aminocapronitrile (ACN) and a stream of water are introduced into a mixer. The molar ratio of water to ACN is preferably maintained in the range of about 1 to 10. The ACN stream can contain about 0 to 1000 ppm tetrahydroazepine (THA) and about 0 to 1 wt % dimer of ACN. The ACN stream and water stream should contain less than 0.1 wt % dissolved oxygen which can be accomplished by blanketing the ACN and water with nitrogen prior to feeding to the mixer. The mixer intimately mixes the ACN stream and water stream. A static mixer, such as a Kenix® mixer, can be used. A mixture of ACN and water is produced by the mixer and then is introduced into a vaporizer. Heat is supplied to vaporize the ACN/water mixture to produce a vapor mixture of ACN and steam. Electrical heating, process to process heat transfer, steam or a hot oil system, using a suitable heat transfer fluid such as a material sold by Dow Chemical Company under the trademark "Dowtherm-A" can be used to supply the heat. The ACN/steam vapor mixture is introduced into a superheater in which the ACN/steam vapor mixture is further heated to a temperature in the range of about 220° C. to about 300° C. to produce a superheated mixture of ACN/steam vapor. Electrical heating, process to process heat transfer, high-pressure steam or a hot oil system, using a suitable heat transfer fluid such as a material sold by Dow Chemical Company under the trademark "Dowtherm-A," can be used to supply heat to the superheater.

The superheated ACN/steam vapor is then introduced into the first of a plurality of successive adiabatic reaction zones. Each reaction zone contains a catalyst. For purposes of illustration only and not to be limiting, a system may comprise five (5) successive adiabatic reaction zones, specifically a first reaction zone, a second reaction zone, a third reaction zone, a fourth reaction zone and a final reaction zone. As few as two (2) or as many as ten (10) or more reaction zones can be used according to the invention. The reaction zones can be of the same size or different size, i.e. the amount of catalyst can be the same or different in different reaction zones. In a preferred version, the amount of catalyst in each reaction zone increases through successive reaction zones, with the smallest amount of catalyst found in the first reaction zone and the largest amount of catalyst found in the final as reaction zone. The reaction zones may be of any diameter. The reaction zones should be well insulated to minimize heat loss. The reaction zones can be equipped with temperature sensors, e.g., thermocouples to measure temperature at different locations inside the reaction zones. The catalyst is preferably a solid acid catalyst.

Solid acids are defined as those materials that have protons or coordinately unsaturated cationic centers on their surface (*Catalysis of Organic Reactions by Supported Inorganic Reagents* by James H. Clark, VCH Publishers, Inc., N.Y., 1994). Based on the above definition, solid acid catalysts are broadly classified into two categories, namely Brønsted Acids and Lewis Acids. The former tends to donate a proton, while the latter shows the tendency to accept an electron pair (*New Solid Acids and Bases—Their Catalytic Properties*, by Tanabe, K., Misono, M., Ono, Y., and Hattori, H., Elsevier, 1989). Examples of suitable solid Brønsted Acids are:

1. Simple oxides (e.g. silica, alumina, titania, etc.);
2. Mixed oxides (e.g. silica-alumina, zeolites, etc.);
3. Natural and synthetic clay minerals (e.g. montmorillonite, etc.);
4. Supported acids (e.g. sulfuric acid-silica, sulfated zirconia, fluorinated alumina, etc.); and
5. Solids containing activated water molecules (e.g. hydrated sulfates, etc.).

Yttrium triflate and aluminum chloride on silica are examples of suitable solid Lewis Acid catalysts.

In the embodiment of the present invention in which a solid acid catalyst is used, the hydrolytic cyclization reaction may occur on the surface of the catalyst. Reactions that are predominantly surface-catalyzed may lead to non-selective intermolecular reactions in addition to the desired hydrolytic cyclization reaction. The intermolecular reactions typically give rise to oligomeric byproducts. However, in the case of microporous solid acid catalysts (e.g. zeolites), cyclization reactions are favored over the intermolecular reactions due to the shape and size of the pores and the nature of absorption of the reactant or intermediate moiety inside the pores of the solid acid catalyst. The pores of the solid acid catalyst are preferably sized so that they allow diffusion of the reactant and product moieties yet restrict the formation of larger molecules as a result of intermolecular reactions. In the microporous solid acid catalysts, the intermolecular reactions can be further suppressed by passivating the external surface of the solid acid catalyst.

Preferred solid acid catalysts suitable for use in this invention are selected from the group consisting of γ-alumina, silica, and titania, as disclosed in U.S. Pat. Nos. 6,262,259; 4,625,023; and 6,353,101. γ-alumina is a preferred solid acid catalyst. The catalyst can be in the form of beads, pellets or extrudates. Typically, each system uses only one catalyst throughout the system, although this is not intended to be limiting in any way.

The superheated ACN/steam vapor enters the first reaction zone. Upon contact with the catalyst therein, at least a portion of the ACN undergoes a hydrolytic cyclization reaction that produces ε-caprolactam. A first reaction product is produced in the first reaction zone, which comprises unreacted ACN, unreacted water and CPL. The hydrolytic cyclization reaction is exothermic and therefore the temperature of the contents of the first reaction zone increases as a result of the reaction. Accordingly, the temperature of the first reaction product is greater than the temperature of the superheated ACN/steam vapor that entered the first reaction zone. The rise in temperature is dependent on the heat of reaction, the amount of catalyst in the first reaction zone, temperature, flow rate and molar ratio of ACN to water in the superheated ACN/steam vapor entering the first reaction zone.

The first reaction product is then introduced into a first cooling device in which heat is removed from the first reaction product to produce a cooled first reaction product. The first cooling device can be a heat exchanger.

The cooled first reaction product is then introduced into a second reaction zone. In the second reaction zone, upon contact with the catalyst therein, at least a portion of the ACN in the cooled first reaction product undergoes hydrolytic cyclization to produce CPL and heat of reaction. A second reaction product, comprising unreacted ACN, unreacted water, CPL and ammonia, is produced. The temperature of the second reaction product is greater than the temperature of the cooled first reaction product that entered the second reaction zone. The second reaction product is then introduced into a second cooling device in which heat is removed from the second reaction product to produce a cooled second reaction product.

The cooled second reaction product is then introduced into a third reaction zone. In this third reaction zone, upon contact with the catalyst therein, at least a portion of the ACN in the cooled second reaction product undergoes hydrolytic cyclization to produce CPL and heat of reaction. A third reaction product comprising unreacted ACN, unreacted water, ammonia, and CPL is produced and withdrawn from the third reaction zone. The temperature of the third reaction product is greater than that of the cooled second reaction product that entered the third reaction zone. The third reaction product is introduced into a third cooling device in which heat is removed from the third reaction product to produce a cooled third reaction product.

The cooled third reaction product is introduced into a fourth reaction zone. In this fourth reaction zone, upon contact with the catalyst therein, at least a portion of the ACN in the cooled third reaction product undergoes hydrolytic cyclization to produce CPL and heat of reaction. A fourth reaction product comprising unreacted ACN, unreacted water, ammonia, and CPL is produced and withdrawn from the fourth reaction zone. The temperature of the fourth reaction product is greater than that of the cooled third reaction product that entered the fourth reaction zone. The fourth reaction product is introduced into fourth cooling device in which heat is removed from the fourth reaction product to produce a cooled fourth reaction product.

The cooled fourth reaction product is introduced into the final reaction zone. In this final reaction zone, upon contact with the catalyst therein, at least a portion of the ACN in the cooled fourth reaction product undergoes hydrolytic cyclization to produce CPL and heat of reaction. A final reaction product comprising unreacted ACN, unreacted water, ammonia, and CPL is produced and withdrawn from the final reaction zone.

The five reaction zones and the four interstage cooling devices are operated in a way that the temperature of the final reaction product is in the range of about 225° C. to about 350° C., preferably about 250° C. to about 325° C. Those skilled in the art can determine how much cooling should be performed by each interstage cooling device in order to meet these temperature ranges. The reactions are generally carried out at a pressure from about 0.01 to about 10 bar absolute (about 1 to about 1000 kPA), preferably between about 1 to about 3 bar absolute (about 100 to about 300 kPa). The reactions may be carried out in the presence of an inert gas, for example argon or nitrogen, in which case the inert gas may be present in an excess of up to 100-fold based on the aminonitrile.

The five reaction zones and the four inter-stage cooling devices can be separate vessels or any two or more successive reaction zones with inter-stage cooling can be integrated into one large vessel.

The final reaction product is then introduced into a distillation column. A distillate comprising ammonia, water, and low boilers is separated from a column tails comprising CPL, ACN, water, and high boilers. The distillation column typically contains structured packing. The distillation column operates in a way that the distillate is preferably removed at a temperature of about 97° C. and the column tails are preferably maintained at a temperature greater than about 100° C. The distillation column is preferably operated at atmospheric pressure and at a reflux ratio of about 0.1 to 10.0, preferably at about 0.45 to 0.75. The vapor feed exiting the final reaction zone is usually induced substantially into the middle of the distillation column.

The weight hourly space velocity (WHSV) of the ACN is typically within the range from about 0.1 to about 5 g ACN per g of catalyst per hour, preferably within the range from about 0.5 to about 2.0 g ACN per g of catalyst per hour. Conversions based on ACN are within the range from about 70 to 99.9%, preferably above 90%. The selectivity of CPL formation is generally above 85%, preferably above 90%, particularly preferably above 95%. These conversion and selectivity values can be achieved for a catalyst life of greater than 750 g CPL produced per g of catalyst.

In a system of a second embodiment of the present invention, an ACN stream and a water stream are introduced into a mixer. The molar ratio of water to ACN is preferably maintained in the range of about 1:1 to 10:1. The ACN stream can contain about 0 to 1000 ppm tetrahydroazepine (THA) and about 0 to about 1 wt. % dimer of ACN. The ACN stream and water stream should contain less than about 0.1 wt % dissolved oxygen which can be accomplished by blanketing the ACN and water with nitrogen prior to feeding to the mixer. The mixer intimately mixes the ACN stream and water stream. A static mixer, such as a Kenix® mixer, can be used. A mixture of ACN and water is produced by the mixer and then is introduced into a vaporizer. Heat is supplied to vaporize the ACN/water mixture to produce a vapor mixture of ACN and steam. Electrical heating, process to process heat transfer, steam or a hot oil system, using a suitable heat transfer fluid such as a material sold by Dow Chemical Company under the trademark "Dowtherm-A," can be used to supply the heat. The ACN/steam vapor mixture is introduced into a superheater in which the ACN/steam vapor mixture is further heated to a temperature in the range of about 220° C. to about 300° C. to produce a superheated mixture of ACN/steam vapor. Electrical heating, process to process heat transfer, high-pressure steam or a hot oil system, using a suitable heat transfer fluid such as a material sold by Dow Chemical Company under the trademark "Dowtherm-A," can be used to supply heat to the superheater.

The superheated ACN/steam vapor is then introduced into the first of a plurality of a successive adiabatic reaction zones. Each reaction zone contains a catalyst. For purposes of illustration only and not to be limiting, a system may comprise five (5) successive adiabatic reaction zones, specifically a first reaction zone, a second reaction zone, a third reaction zone, a fourth reaction zone and a final reaction zone. As few as two (2) or as many as ten (10) or more reaction zones can be used according to the invention. The reaction zones can be of the same size or different size, i.e. the amount of catalyst can be the same or different in different reaction zones. In a preferred version, the amount of catalyst in each reaction zone increases through successive reaction zones, with the smallest amount of catalyst found in the first reaction zone and the largest amount of catalyst found in the final reaction zone. The diameter of the reaction zones is not critical. The reaction zones should be well insulated to minimize heat loss. The reaction zones can be equipped with temperature sensors, e.g. thermocouples to measure temperature at different locations inside the reaction zones. The catalyst is preferably a solid acid catalyst, as previously described.

The superheated ACN/steam vapor enters the first reaction zone. Upon contact with the catalyst therein, at least a portion of the ACN undergoes a hydrolytic cyclization reaction that produces ε-caprolactam. A first reaction product is produced in the first reaction zone, which comprises unreacted ACN, unreacted water and CPL. The hydrolytic cyclization reaction is exothermic and therefore the temperature of the contents of the first reaction zone increases as a result of the reaction. Accordingly, the temperature of the first reaction product is greater than the temperature of the superheated ACN/steam vapor that entered the first reaction zone. The rise in temperature is dependent on the heat of reaction, the amount of catalyst in the first reaction zone, temperature, flow rate and molar ratio of ACN to water in the superheated ACN/steam vapor entering the first reaction zone.

The first reaction product is introduced into a first cooling device in which a cold shot liquid is added to the first reaction product to produce a cooled first reaction product. The first cooling device can be a separate mixing vessel or an integral part of the first reaction zone. The cold shot liquid can be selected from the group consisting of water, methanol, ethanol, 6-aminocapronitrile, ε-caprolactam, ammonia, hexamethylene diamine, and mixtures of two or more of these compounds. A preferred cold shot liquid is water. Cooling by the sensible-heat removal from the first reaction product is accomplished by the latent heat required for vaporization of the cold shot liquid. Because the change in specific enthalpy required to cool the reaction product is a fraction of the change in specific enthalpy required to vaporize the cold shot liquid the required quantity of cold shot liquid is small in comparison to the quantity of first reaction product.

The cooled first reaction product is then introduced into a second reaction zone. In this second reaction zone, upon contact with the catalyst therein, at least a portion of the ACN in the cooled first reaction product undergoes hydrolytic cyclization to produce CPL and heat of reaction. A second reaction product comprising unreacted ACN, unreacted water, ammonia, and CPL is produced. The temperature of the second reaction product is greater than that of the cooled first reaction product that entered the second reaction zone. The second reaction product is introduced into a second cooling device in which a cold shot liquid as described above is added to the second reaction product to produce a cooled second reaction product.

The cooled second reaction product is introduced into a third reaction zone. In this third reaction zone, upon contact with the catalyst therein, at least a portion of the ACN in the cooled second reaction product undergoes hydrolytic cyclization to produce CPL and heat of reaction. A third reaction product comprising unreacted ACN, unreacted water, ammonia, and CPL is produced. The temperature of the third reaction product is greater than that of the cooled second reaction product that entered the third reaction zone. The third reaction product is introduced into a third cooling device in which a cold shot liquid, as previously described, is added to the third reaction product to produce a cooled third reaction product.

The cooled third reaction product is introduced into a fourth reaction zone. In this fourth reaction zone, upon contact with the catalyst therein, at least a portion of the ACN in the cooled third reaction product undergoes hydrolytic cyclization to produce CPL and heat of reaction. A fourth reaction product, comprising of unreacted ACN, unreacted water, ammonia, and CPL is produced. The temperature of the fourth reaction product is greater than that of the cooled third reaction product that entered the fourth reaction zone. The fourth reaction product is introduced into a fourth cooling device, in which a cold shot liquid, as described before, is added to the fourth reaction product to produce a cooled fourth reaction product.

As in the first cooling device, the second, third and fourth cooling devices can be separate mixing vessels or integral parts of the second, third and fourth reaction zones, respectively.

The cooled fourth reaction product is introduced into a final reaction zone. In this final reaction zone, upon contact with the catalyst therein, at least a portion of the ACN in the cooled fourth reaction product undergoes hydrolytic cyclization to produce CPL and heat of reaction. A final reaction product comprising unreacted ACN, unreacted water, ammonia, and CPL is produced.

The final reaction zone and the first, second, third and fourth inter-stage cooling devices are operated in a way that the temperature of the final reaction product is in the range of about 225° C. to about 350° C., preferably about 250° C. to about 325° C. Those skilled in the art can determine how much cooling should be performed by each interstage cooling device in order to meet these temperature ranges. The reactions are generally carried out at a pressure from 0.01 to 10 bar absolute (1 to 1000 kPA), preferably between 1 to 3 bar absolute (100 to 300 kPa). The reactions may be carried out in the presence of an inert gas, for example argon or nitrogen, in which case the inert gas may be present in an excess of up to 100-fold based on the aminonitrile.

The final reaction product is then introduced into a distillation column. A distillate comprising ammonia and water is separated from a column tails comprising CPL, ACN, and water. The distillation column typically contains structured packing. The distillation column operates in a way that the distillate is preferably removed at a temperature of about 97° C. and the column tails are preferably maintained at a temperature greater than about 100° C. The distillation column is preferably operated at about atmospheric pressure and at a reflux ratio of about 0.1 to 1.0, preferably at about 0.45 to 0.75. The vapor feed exiting the final reaction zone is usually introduced substantially in the middle of the distillation column.

The weight hourly space velocity (WHSV) of the ACN is typically within the range from 0.1 to 5 g ACN per g of catalyst per hour, preferably within the range from 0.5 to 2.0 g ACN per g of catalyst per hour. Conversions based on ACN are within the range from about 70 to 99.9%, preferably above 90%. The selectivity of CPL formation is generally above 85%, preferably above 90%, particularly preferably above 95%. These conversion and selectivity values can be achieved for a catalyst life of greater than 750 g CPL produced per g of catalyst.

In another embodiment of the invention, a combination of heat exchangers and cold shot liquids can be used to cool the intermediate reaction products between successive reaction zones.

In another embodiment of the invention, at least a small portion of fresh cold ACN can be introduced directly into any reaction stage after the first reaction zone. At least a portion of any intermediate reaction product (before or after cooling by heat exchange or cold shot) can also be introduced directly into any reaction zone after the reaction zone that produced it.

In another embodiment of the present invention, at least a portion of an intermediate reaction product (before or after cooling by heat exchange or cold shot) or at least a portion of the final reaction product after cooling can be recycled back to the inlet of the same reaction zone that produced it or to the inlet of any other reaction zone preceding that reaction zone that produced it.

Deactivation of a catalyst is an integral part of a catalyst lifecycle. Therefore, catalyst regeneration plays an important role in the economics of the overall process. In the present invention, after the catalyst deactivates to a certain level, i.e., the conversion of ACN and/or selectivity of CPL drops below a pre-defined value, the catalyst can be regenerated and its activity and selectivity can be restored to substantially its original value.

When the activity and/or selectivity of the catalyst drops below a predefined value, first the ACN flow can be discontinued, while maintaining the flow of the superheated steam. After running steam through the reactor system for about 1 to 10 hours, preferably for about 2 to 5 hours, the superheater temperature can be adjusted to about 270° C. and then air can be added to the system, preferably before the first reactor, at such a rate so as to control the location of the "hot spot." The "hot spot"is the location in the fixed bed reactor where rapid temperature excursion occurs due to an exothermic reaction. The "hot spot" is thus preferably controlled such that it progressively travels down the length of the reactors beginning with the first reactor. The maximum temperature of the "hot spot" should be controlled between about 500° C. and about 750° C., preferably between about 550° C. and about 700° C., to substantially regenerate the entire catalyst bed, and at the same time to minimize the effect on the activity of the catalyst by high temperature sintering. The regeneration process is typically considered completed when the temperature exotherm in each of the reactors disappears. The air flow is then turned off, wait until the oxygen is sufficiently purged from the system, the superheater temperature adjusted to the desired value and ACN feed is turned on.

It should be appreciated that the following examples are presented to more fully demonstrate and further illustrate various individual aspects and features of the present invention and as such the examples are felt to be non-limiting and are meant to illustrate the invention but are not meant to be unduly limiting in any way.

EXAMPLE 1

The hydrolytic cyclization of ACN was carried out in an integrated five-stage adiabatic reactor system with inter-stage cooling, followed by a distillation column for product separation. The experimental setup is comprised of;

- Two feed drums, one containing distilled water, and the other ACN. Both feed drums were kept under a blanket of nitrogen and sparged with nitrogen to remove dissolved oxygen.
- A vaporizer which consisted of a jacketed 1½ inch stainless steel pipe heated by 140 psig (965 kPa) steam in the jacket. This was fed from the feed drums by two metering (FMI) pumps, A Kenix® mixer was attached in between the vaporizer and FMI pumps to ensure complete mixing of the reactant. A line was attached to the bottom of the vaporizer to take a blow-down purge from the vaporizer, if needed.
- An electrically heated superheater, which took the vapor from the vaporizer and superheated it to the desired inlet temperature of the first reactor.
- Five well-insulated reactors with inter-stage cooling or provision for injecting cooling water into the reactors. The reactors were made from 1½ inch stainless steel pipes. The catalyst bed lengths for stages 1 through 5 were 9, 12, 18, 26 and 84 inches, respectively. The five reactors were charged with 165.4, 272.8, 3640.4, 505.6, and 1429.4 g of γ-alumina catalyst, respectively, in the form of cylindrical extrudates. Heating tapes wrapped around the reactor were manually controlled by powerstats designed to supply the heat lost through the insulation of the reactor, which can be substantial at this very small experimental scale where surface area to volume ratios are significantly larger than at commercial manufacturing scale. A thermowell was installed down the length of the first four reactors, which contained two multi-point thermocouples to measure twenty temperatures down the reactor length. The fifth reactor contained one internal thermocouple at each end of the reactor to monitor the inlet and exit temperatures. A heated transfer line that acted as a cooler connected the fourth and the fifth reactors.

The reactors were charged with ⅛" cylindrical extrudates of γ-alumina catalyst obtained from Degussa (apparent bulk density of 0.7551 g/cm$^3$; and BET surface area of 350 m$^2$/g). The feed comprised 30 g/min of ACN and 30 g/min of water, WHSV of 1.0 hr$^{-1}$. The system ran with inlet/exit temperatures of the five reactors at approximately 295° C./307° C., 302° C./307° C., 288° C./312° C., 296° C./300° C., and 260° C./290° C., respectively, for a total time on stream of 8 hours. The system ran at a pressure of slightly above 1 atm.

The outlet from the fifth reactor was connected to the inlet of a distillation column. The vapor feed from the outlet of the fifth reactor was fed to substantially the middle of the distillation column, which was maintained at atmospheric pressure. The distillation column separated ammonia, water, and low boiling impurities from the reaction products comprising of CPL, ammonia, water, unconverted ACN, and small quantities of other low and high boiling impurities eluting from the five-stage reactor system.

Ammonia, water, and low boiling impurities were condensed in a condenser attached to the top of the (Oldershaw column) and a variable portion returned to the top of the column as reflux to maintain a condenser temperature of 97° C. (reflux ratio of 0.65). The top of the condenser was connected to the vent header to discharge small quantities of non-condensible gases/vapors emanating from the distillation column.

CPL, water, and other high boiling components (impurities) were collected in the reboiler (or pot) at the bottom of the Oldershaw column. The liquid product, containing CPL and approximately 25 wt. % water, was continuously removed from the reboiler by a metering (FWI) pump and collected in a 55 gallon drum. The analyses of the liquid product showed 99.6% selectivity to CPL and an overall ACN conversion of 95%. The resultant 94.6% yield of CPL remained approximately constant for the total duration of the 8-hour run. The analyses of the liquid product did not show any significant change in the impurity level compared to that at the exit of the fifth reactor.

EXAMPLE 2

In a manner analogous to Example 1 a second run was performed essentially under identical conditions except the feed composition was reduced to 20 g/min of ACN and 20 g/min of water. The analyses of the product collected in the reboiler/pot of the Oldershaw column showed 99.6% selectivity to CPL and an overall ACN conversion of 98.7%. The resultant 98.3% yield of CPL remained approximately constant for the total duration of the 7-hour run. The analyses of the product did not show any significant change in the impurity level compared to that at the exit of the fifth reactor.

What is claimed is:

1. A process for preparing ε-caprolactam (CPL) by the hydrolytic cylization of 6-aminocapronitrile (ACN) in the vapor phase, said process comprising:
   (a) contacting a superheated mixture of 6-aminocapronitrile vapor and steam with a catalyst in a plurality of adiabatic reaction zones arranged in succession and containing the catalyst, beginning with a first reaction zone and terminating with a final reaction zone, wherein the superheated vapor mixture is fed into the first reaction zone, and a final reaction product comprising CPL is removed from the final reaction zone, and from each reaction zone prior to the final reaction zone an intermediate reaction product is withdrawn, cooled and then fed into the next reaction zone; and
   (b) separating the CPL from the final reaction product by distillation.

2. The process of claim 1 wherein the 6-aminocapronitrile in the feed mixture contains about 0 to about 1000 ppm tetrahydroazepine and about 0 to about 1 wt % dimer of 6-aminocapronitrile.

3. The process of claim 1 wherein the molar ratio of water to 6-aminocapronitrile in the feed mixture is in the range of about 1:1 to 10:1.

4. The process of claim 1 wherein cooling of at least one of the intermediate reaction products comprises heat exchange.

5. The process of claim 1 wherein cooling of at least one of the intermediate reaction products comprises addition of a cold shot liquid to at least one of the intermediate reaction products, wherein the cold shot liquid is selected from the group consisting of water, methanol, ethanol, ammonia, 6-aminocapronitrile, CPL, hexamethylene diamine, and mixtures of two or more of these compounds.

6. The process of claim 1, comprising a first adiabatic reaction zone and a final adiabatic reaction zone.

7. The process of claim 1, comprising a first adiabatic reaction zone, a final adiabatic reaction zone and at least 3 successive adiabatic reaction zones.

8. The process of claim 7, comprising at least 8 successive adiabatic reaction zones.

9. The process of claim 1 wherein the feed mixture of 6-aminocapronitrile vapor and steam is made by a process comprising:
   (a) mixing 6-aminocapronitrile with water;
   (b) vaporizing the mixture of 6-aminocapronitrile and water; and
   (c) heating the vaporized 6-aminocapronitrile and water to a temperature in the range of about 220° C. to about 300° C.

10. The process of claim 1 further comprising:
   (a) discontinuing the flow of the feed mixture of 6-aminocapronitrile and water vapor through the first adiabatic reaction zone, the successive adiabatic reaction zones and the final adiabatic reaction zone when less than about 95% of the 6-aminocapronitrile in the feed mixture is converted to CPL in the final reaction product;
   (b) contacting the catalyst in the first adiabatic reaction zone, the successive adiabatic reaction zones and the final adiabatic reaction zone with steam; and then
   (c) contacting the catalyst in the first adiabatic reaction zone, the successive adiabatic reaction zones and the final adiabatic reaction zone with a mixture of air and steam.

11. The process of claim 10 wherein in step (b) the catalyst is contacted with steam for about 1 to about 10 hours.

12. The process of claim 11 wherein in step (b) the catalyst is contacted with steam for about 2 to about 5 hours.

13. The process of claim 10 wherein in step (b) the steam is at a temperature of about 270° C.

14. The process of claim 10 wherein in step (c) the maximum temperature in any of the first adiabatic reaction zone, the successive adiabatic reaction zones and the final adiabatic reaction zone does not exceed about 750° C.

15. The process of claim 14 wherein in step (c) the maximum temperature in any of the first adiabatic reaction zone, the successive adiabatic reaction zones and the final adiabatic reaction zone is in the range of about 550° C. to about 700° C.

16. The process of claim 1, wherein the catalyst comprises a solid acid catalyst.

17. The process of claim 16, wherein the solid acid catalyst is selected from the group consisting of Brønsted Acids and Lewis Acids.

18. The process of claim 17, wherein the solid acid catalyst is selected from the group consisting of silica, alumina, titania, silica-alumina, zeolites, montmorillonite, sulfuric acid-silica sulfated zirconia, fluorinated alumina, hydrated sulfate, yttrium triflate and aluminum chloride on silica.

19. The process of claim 18, wherein the solid acid catalyst comprises γ-alumina.

20. The process of claim 1, comprising greater than about 90% conversion of the 6-aminocapronitrile in the feed mixture to CPL.

21. The process of claim 1, wherein the exit temperature of at least one adiabatic reaction zone is at least about 5° C. higher than the inlet temperature of said adiabatic reaction zone.

22. The process of claim 21, wherein the exit temperature of at least one adiabatic reaction zone is at from about 5° C. to about 30° C. higher than the inlet temperature of said adiabatic reaction zone.

23. The process of claim 20, wherein the exit temperature of at least one adiabatic reaction zone is at least about 5° C. higher than the inlet temperature of said adiabatic reaction zone.

24. The process of claim 23, wherein the exit temperature of at least one adiabatic reaction zone is at from about 5° C. to about 30° C. higher than the inlet temperature of said adiabatic reaction zone.

* * * * *